United States Patent
Sassak et al.

(10) Patent No.: US 6,817,992 B1
(45) Date of Patent: Nov. 16, 2004

(54) MALE INCONTINENCE GARMENT

(76) Inventors: Diane Sassak, 10239 Dupage Ave., Las Vegas, NV (US) 89135; Deborah Sassak, 800 Hawk Dr., Walled Lake, MI (US) 48390

( * ) Notice: Subject to any disclaimer, the term of this patent is extended or adjusted under 35 U.S.C. 154(b) by 17 days.

(21) Appl. No.: 10/335,412

(22) Filed: Dec. 31, 2002

(51) Int. Cl.[7] .............................. A61F 13/20; A61F 5/44
(52) U.S. Cl. ................................... 604/385.09; 604/349
(58) Field of Search ....................... 604/385.01, 385.03, 604/385.04, 385.09, 385.14, 385.19, 387, 349, 348, 351

(56) References Cited

U.S. PATENT DOCUMENTS

| | | | |
|---|---|---|---|
| 3,356,091 A | * 12/1967 | Patterson | 604/348 |
| 3,613,123 A | 10/1971 | Langstrom | |
| 4,553,968 A | 11/1985 | Komis | |
| 4,559,051 A | * 12/1985 | Hanson | 604/385.03 |
| 4,813,943 A | 3/1989 | Smith | |
| 4,955,088 A | 9/1990 | Terjesen | |
| 5,009,649 A | * 4/1991 | Goulter et al. | 604/351 |
| 5,074,853 A | 12/1991 | Bryant | |
| 5,300,052 A | 4/1994 | Kubo | |
| 5,586,978 A | 12/1996 | Bayne | |
| 5,618,279 A | * 4/1997 | Pudlo | 604/385.09 |
| 5,651,778 A | * 7/1997 | Melius et al. | 604/385.19 |
| 5,707,364 A | * 1/1998 | Coates | 604/391 |
| 5,716,350 A | * 2/1998 | Ryan | 604/385.09 |
| 6,059,762 A | 5/2000 | Boyer et al. | |
| 6,113,582 A | 9/2000 | Dwork | |
| 6,114,597 A | * 9/2000 | Romare | 604/378 |
| 6,209,142 B1 | 4/2001 | Mattsson | |
| 6,248,096 B1 | 6/2001 | Dwork et al. | |
| 6,562,016 B2 | * 5/2003 | Shinkai | 604/385.01 |
| 6,569,135 B1 | * 5/2003 | Mula | 604/349 |
| 6,579,273 B2 | * 6/2003 | Dupuy | 604/385.14 |
| 6,623,465 B1 | * 9/2003 | Roe et al. | 604/385.03 |
| 6,685,687 B2 | * 2/2004 | Mishima et al. | 604/385.19 |
| 2002/0138058 A1 | * 9/2002 | Mishima et al. | 604/385.19 |
| 2003/0028161 A1 | * 2/2003 | Carballo | 604/349 |

* cited by examiner

*Primary Examiner*—John J. Calvert
*Assistant Examiner*—Michael Bogart
(74) *Attorney, Agent, or Firm*—Carrier, Blackman & Associates, P.C.; William D. Blackman; Joseph P. Carrier

(57) ABSTRACT

A disposable diaper includes a main diaper body with a flexible plastic housing. The diaper housing has a front wall and a parallel back wall sealably joined to the front wall. The front and back walls cooperate to define a housing chamber therebetween. The back wall has an aperture formed therein. The main diaper body also includes at least one layer of absorbent material disposed within the housing chamber. The diaper also includes a flexible sleeve for surrounding a user's phallus. The flexible sleeve attached to the back wall of the housing around the aperture, and is in fluid communication with the housing chamber via the aperture. The diaper may have an adhesive material attached to a lower portion of the front wall, to allow it to be removably fastened to an undergarment.

15 Claims, 7 Drawing Sheets

MALE INCONTINENCE GARMENT

BACKGROUND OF THE INVENTION

1. Field of the Invention

The present invention relates to disposable diapers for incontinent males, and to a garment system incorporating same. More particularly, the present invention relates to a leak-resistant disposable diaper including a main fluid-absorbing diaper body and a flexible sleeve, attached to the main diaper body, for directing fluid flow into the interior of the diaper.

2. Description of the Background Art

A number of different absorbent pads and related devices are known for dealing with male incontinence. Examples of some of the known devices include U.S. Pat. No. 3,613,123 to Langstrom, U.S. Pat. No. 4,553,968 to Komis, U.S. Pat. No. 4,813,943 to Smith, U.S. Pat. No. 5,074,853 to Bryant, U.S. Pat. No. 5,300,052 to Kubo, U.S. Pat. No. 5,586,978 to Bayne, U.S. Pat. No. 6,059,762 to Boyer et al., U.S. Pat. No. 6,113,582 to Dwork, U.S. Pat. No. 6,209,142 to Mattson, and U.S. Pat. No. 6,248,096 to Dwork et al.

U.S. Pat. No. 4,955,088 to Terjesen discloses a design for a specialized male undergarment, containing an extra rectangular section of fabric forming a pouch between the leg portions.

Although the known diapers have some utility for their intended purposes, a need still exists in the art for an improved leak-resistant diaper for incontinent male users. In particular, there is a need for an improved diaper for male users which is structured to reliably catch and trap fluid waste, while tending to keep such fluid away from the user's skin. Furthermore, there is a need for a garment system including such a specialized leak-resistant diaper.

SUMMARY OF THE INVENTION

The present invention provides an improved diaper for male users which is structured to reliably catch and trap fluid waste, while keeping such fluid away from the user's skin.

In a first illustrative embodiment of the invention, a disposable diaper includes a main diaper body with a flexible plastic housing. The diaper housing has a front wall and a back wall sealably joined to the front wall and substantially parallel thereto. The back wall has an aperture formed therein. The front and back walls cooperate to define a housing chamber therebetween.

The main diaper body also includes at least one layer of absorbent material disposed within the housing chamber.

The diaper also includes a flexible sleeve, attached to the back wall of the housing surrounding the aperture. The sleeve is substantially cylindrical in shape, although flexible, and is substantially perpendicular to the back wall of the housing. The flexible sleeve is in fluid communication with the housing chamber via the aperture. The sleeve is provided for placement surrounding a user's phallus, to direct inadvertent fluid flow into the interior of the housing.

Optionally, the diaper may have an adhesive material attached to a lower portion of the housing front wall, to allow it to be removably fastened to an undergarment.

The main diaper body may also include a first flange extending outwardly at an upper left portion thereof, and a second flange extending outwardly at an upper right portion thereof. Where these side flanges are used, a fastener may be provided, attached to each of the flanges, for fastening the diaper to an undergarment.

Accordingly, it is an object of the present invention to provide an improved diaper for use by incontinent males.

For a more complete understanding of the present invention, the reader is referred to the following detailed description section, which should be read in conjunction with the accompanying drawings. Throughout the following detailed description and in the drawings, like numbers refer to like parts.

DETAILED DESCRIPTION OF THE PREFERRED EMBODIMENTS

First Embodiment

Figure 1:
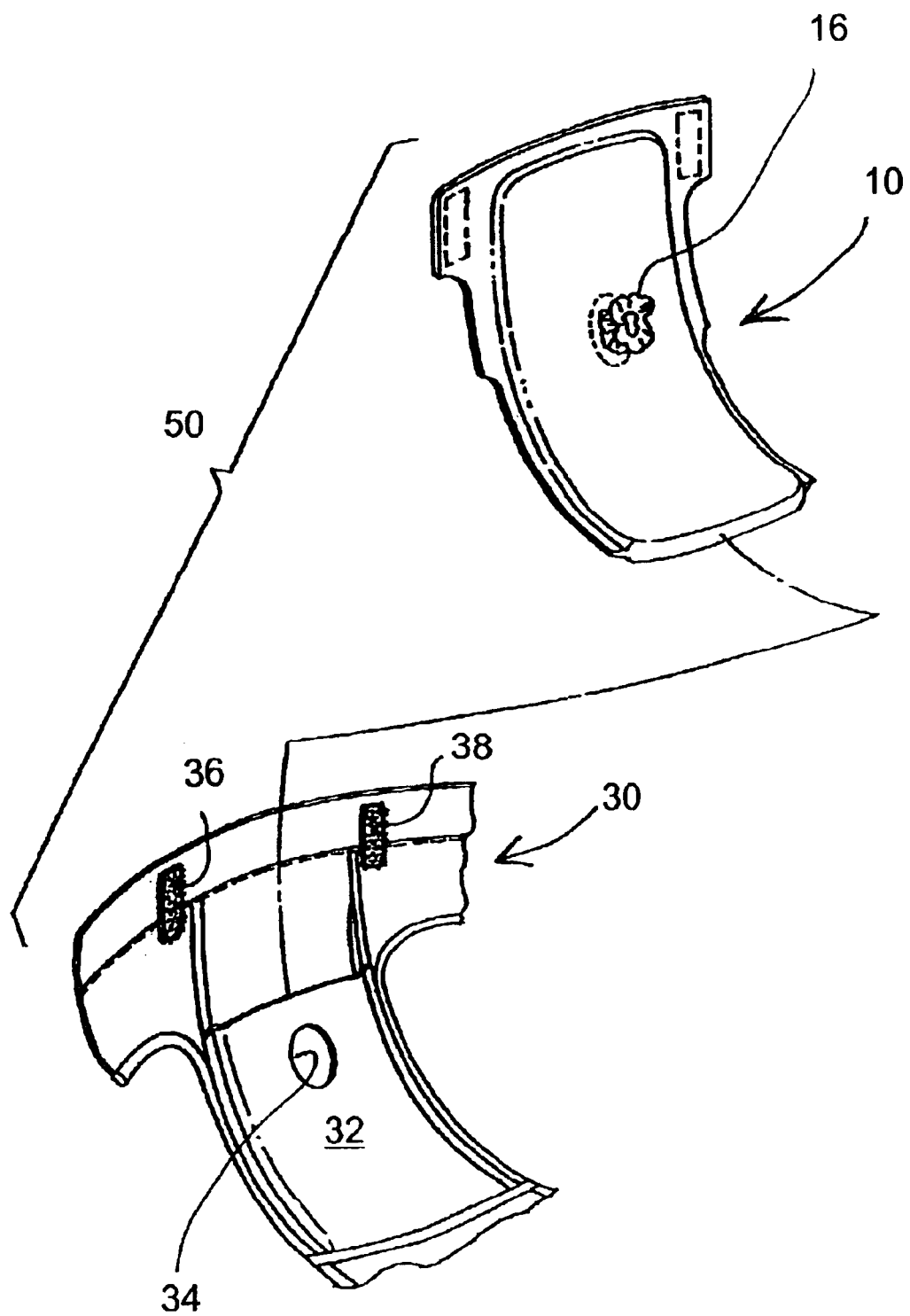
FIG. 1 is an exploded perspective view of a diaper and garment system according to a first embodiment hereof.

Referring now to FIGS. 1–4 of the drawings, a leak-resistant disposable diaper according to a first embodiment of the invention is shown generally at 10. In the embodiment of FIGS. 1–4, the diaper 10 is usable in conjunction with a specialized undergarment 30, to make up a leak control system 50 according to the present invention. While the diaper 10 of FIGS. 1–4 is usable with a specialized undergarment 30, as part of a leak control system 50, it will be understood that alternatively, the diaper 10 may also be used with a conventional undergarment, and the specialized undergarment 30 is not required in the practice of the invention.

The diaper 10 includes a main diaper body 11 (FIG. 2), and a substantially cylindrical flexible sleeve 16 attached to the main diaper body and in fluid communication with the interior thereof.

Structure of the Diaper Housing

Figure 3:
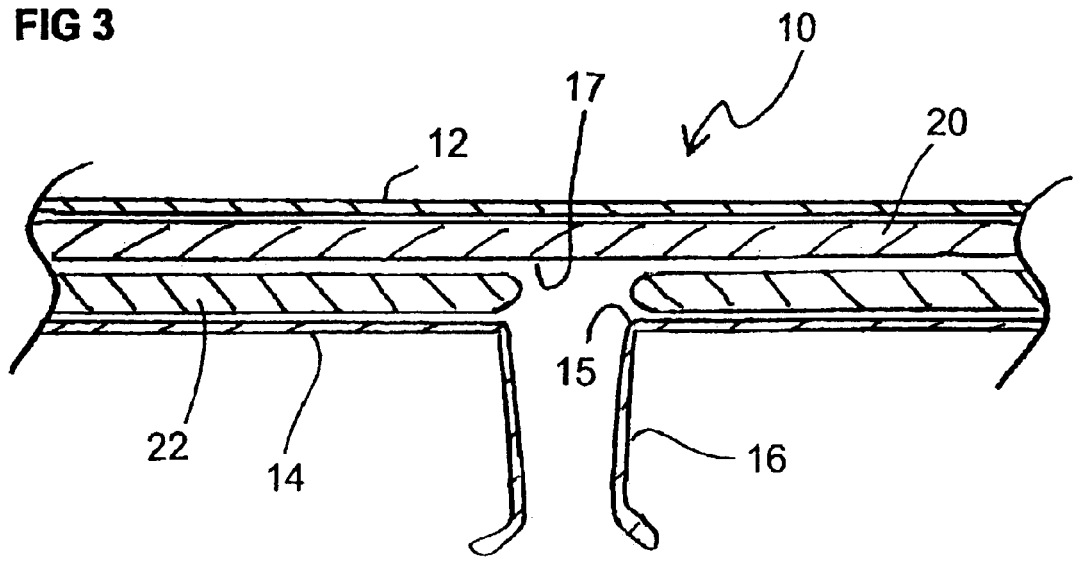
FIG. 3 is a cross-sectional view of the diaper of FIG. 2, taken along the line 3—3.

The main diaper body 11 includes a housing 13 having a front wall 12, and a back wall 14 which is sealably attached to the front wall around the outer periphery of the main diaper body. The front wall 12 is substantially parallel to the back wall 14 in a stored configuration thereof before use, as shown in FIG. 3. The front and back walls 12, 14 cooperate to define a housing chamber 17 therebetween.

Optionally, a lower part of the front wall 12 may have an adhesive material 19 thereon (FIG. 4), such as two-sided adhesive tape or the like. This adhesive material 19 may be covered by a peelably removable strip. Where used, such adhesive material 19 permits the lower part of the diaper 10 to be removably attached to an undergarment, such as the briefs shown at 30.

The back wall 14 of the diaper 10 has an aperture 15 formed therethrough, and the flexible sleeve 16 is attached to the back wall 14, adjacent the aperture 15. Optionally, a part of the sleeve 16 may continue inside of the housing chamber 17.

The Diaper Sleeve

The sleeve 16 is provided for placement surrounding a user's phallus 18, in order to control and direct any leakage of urine therefrom while the user is wearing the diaper 10. The sleeve 16 is in fluid communication with the housing chamber 17 via the aperture 15. As noted, the sleeve 16 is substantially cylindrical in shape, although flexible, and is substantially perpendicular to the back wall of the housing.

The sleeve 16 is provided to direct a user's phallus 18 toward the interior of the diaper 10 to control the direction of fluid flow therefrom, and to thereby minimize unwanted leakage, which may cause rashes, chaffing and other problems if left uncontrolled. Such placement of the sleeve 16 helps ensure that unintentional fluid leakage is directed into the interior of the main diaper body 11. This is especially important for men who experience bladder control problems, or for men who are not able to regularly get to a bathroom such as, for example, pilots of small planes or long-distance truck drivers.

The sleeve 16 is formed from a flexible material, which may include a fluid-resistant plastic, or alternatively, may include a fabric material. The sleeve 16 may further include an elastic material, as illustrated in FIG. 3, in order to cause it to fit closely about the phallus 18 so that it is retained thereon, thereby minimizing the risk of leakage.

Additional Diaper Features

Figure 2:
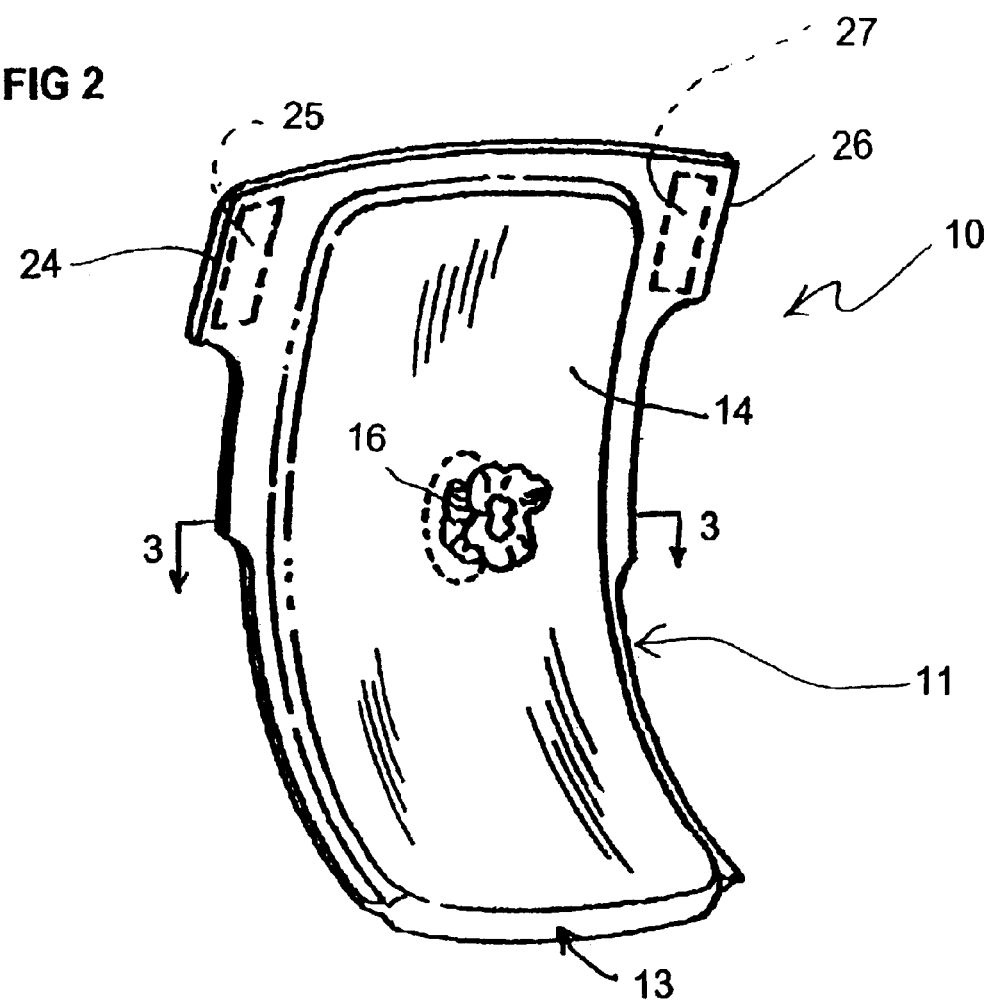
FIG. 2 is a perspective view of a diaper according to the embodiment of FIG. 1.

The diaper 10 also includes at least one layer of absorbent material inside of the housing chamber 17. In the embodiment of FIGS. 1–3, the diaper 10 includes both a first layer 20 of absorbent material next to the front wall 12, and a second layer 22 of absorbent material next to the back wall 14. The material making up the absorbent layers 20, 22 may include any known absorbent material such as those used in commercial baby diapers, and may include cotton and/or paper products.

Optionally, the inward-facing surface of each absorbent layer 20, 22 may include a semi-permeable membrane which lets fluid flow in a first direction therethrough into the absorbent material, yet resists allowing fluid flow in the opposite direction, thereby shielding adjacent skin from prolonged fluid contact. Such semi-permeable membranes are known and used in the baby diaper industry.

In the embodiment of FIGS. 1–3, the main diaper body 11 also includes a first flange 24 extending outwardly at an upper left portion thereof, and a second flange 26 extending outwardly at an upper right portion thereof. These flanges 24, 26 may have respective fasteners 25, 27 on the front surfaces thereof for attaching the diaper to an undergarment.

In the embodiment of FIGS. 1–3, a respective hook portion 25, 27 of a hook-and-loop fastener is attached to each of the first and second flanges 24, 26. Corresponding loop portions 36, 38 of the fasteners may be attached to and suitably situated on the undergarment 30 of FIG. 1, as shown, to permit removable attachment of the diaper 10 thereto.

Alternatively, an adhesive patch or a piece of two-sided tape may be used as a fastener on the front surface of each of the flanges 24, 26.

As suggested by the illustration of FIG. 1, any of the above fasteners may be used to attach the diaper 10 to the specialized briefs or undergarment 30 according to the invention.

Structure of the Undergarment

Figure 4:
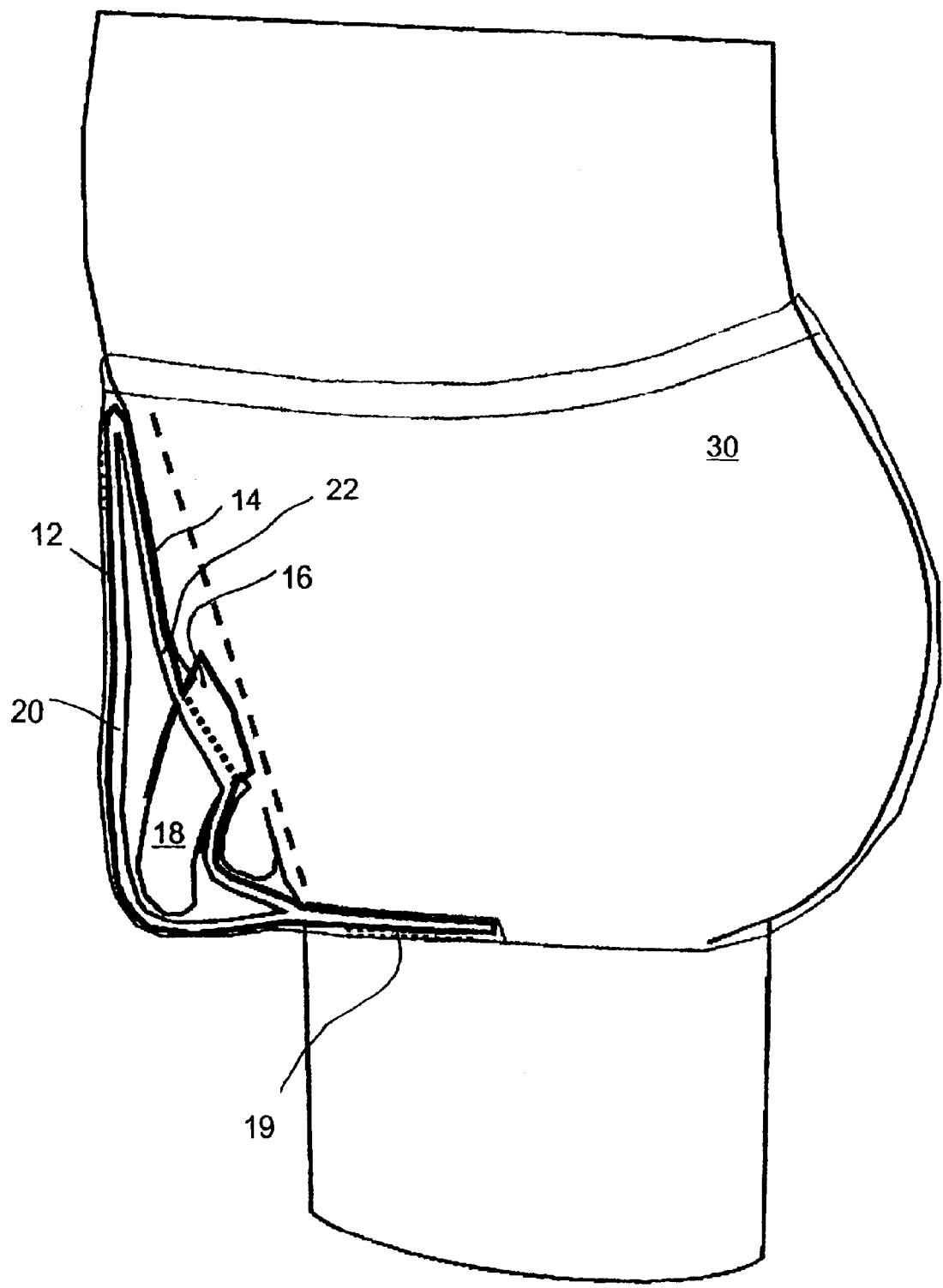
FIG. 4 is a side view, partially in cross-section, of a user wearing the diaper of FIG. 2.

Referring now to FIGS. 1 and 4, the undergarment 30 according to the invention is similar to a normal pair of men's briefs, with the added feature of having an extra pocket 32 attached to the interior center panel thereof. The pocket 32 is sewn to the briefs 30 along seams at the bottom and side edges thereof, but is open at the top, to receive a lower portion of the diaper 10 therein. The pocket 32 may have a hole 34 formed therein to accommodate the sleeve 16, or may be made smaller than that shown, so that the sleeve 16 is not received therein.

Alternate Sleeve Designs

Figure 5:
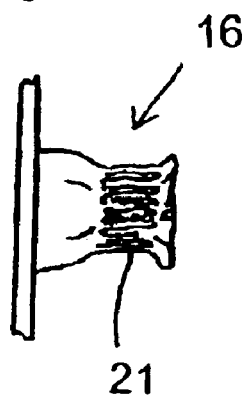
FIG. 5 is a side plan view of a diaper sleeve according to the first embodiment.

A number of different alternative sleeve designs may be used with the diaper 10 hereof, as illustrated in FIGS. 5–8. FIG. 5 illustrates the basic design for the sleeve 16, with the sleeve formed from a flexible plastic or fabric with elastic material 21 incorporated therein.

Figure 6:
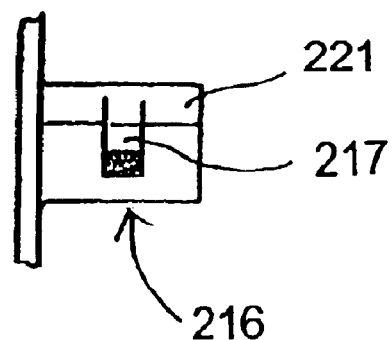
FIG. 6 is a side plan view of a diaper sleeve according to a second embodiment hereof.

FIG. 6 illustrates an alternative design for a sleeve 216 according to a second embodiment of the invention. In this embodiment, the sleeve 216 includes a wrap-around sheet 221 with a fastening strip 217 thereon. The fastening strip 217 may include tape, or the sleeve 216 may incorporate a hook and loop fastener. The remainder of the diaper in the second embodiment, other than the sleeve 216, is the same as that described in connection with the diaper 10 of the first embodiment.

Figure 7:
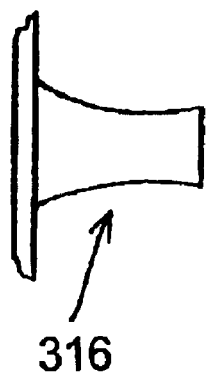
FIG. 7 is a side plan view of a diaper sleeve according to a third embodiment hereof.

FIG. 7 illustrates a third embodiment of a sleeve 316, which is formed from a stretchable material that will return to its original position when released. This material may comprise a fabric, an elastomer, natural latex, and/or another stretchable material. The remainder of the diaper in the third embodiment, other than the sleeve 316, is the same as that described in connection with the diaper 10 of the first embodiment.

Figure 8:
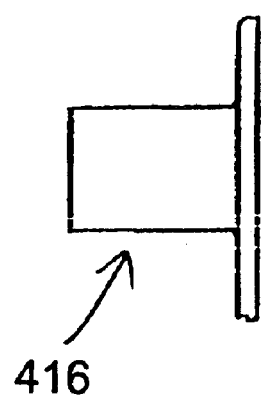
FIG. 8 is a side plan view of a diaper sleeve according to a fourth embodiment hereof.

FIG. 8 illustrates another alternative design for a sleeve 416 according to a fourth embodiment of the invention. In the embodiment of FIG. 8, the sleeve 416 extends inwardly into the interior of the housing chamber 17, instead of extending outwardly from the back wall 14. The remainder of the diaper in the fourth embodiment, other than the sleeve 416, is the same as that described in connection with the diaper 10 of the first embodiment.

Fifth Embodiment

Figure 9:
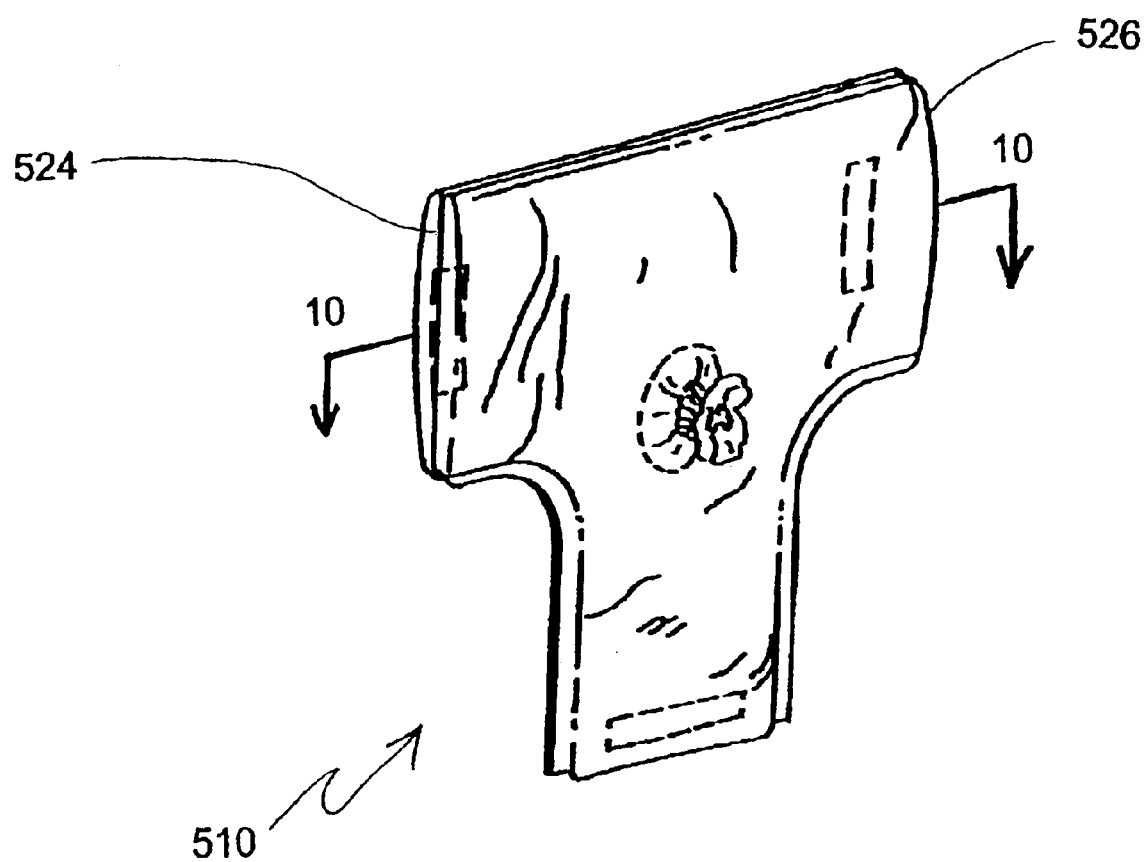
FIG. 9 is a perspective view of a diaper according to a fifth embodiment of the invention.

FIG. 9 illustrates a diaper 510 according to a fifth embodiment of the invention. The diaper 510 according to the fifth embodiment shares many features with the diaper 10 of the first embodiment. Unless described as different herein, it will be understood that the previously described features of the diaper 10 according to the first embodiment carry over, and are also incorporated in the diaper 510 of the fifth embodiment.

Figure 10:
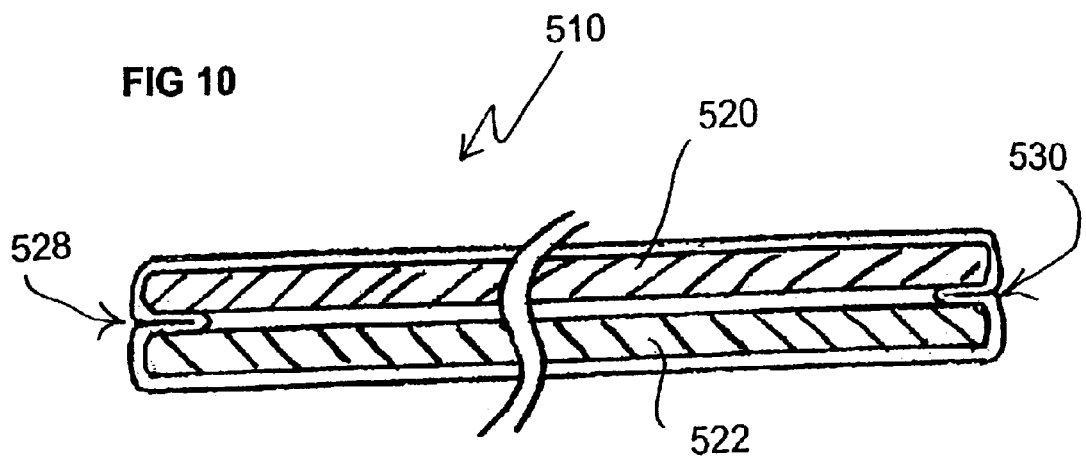
FIG. 10 is a cross-section of the diaper of FIG. 9, taken along the line 10—10.

The diaper 510 according to the embodiment of FIGS. 9–10 includes enlarged side flanges 524, 526, which have absorbent material contained therein. The side flanges 524, 526 are also provided with expandable flutes 528, 530 to provide increased fluid-absorbing capacity. The diaper 510 also includes more absorbent material 520, 522 than is provided in the diaper 10 according to the first embodiment.

Sixth Embodiment

Figure 11:
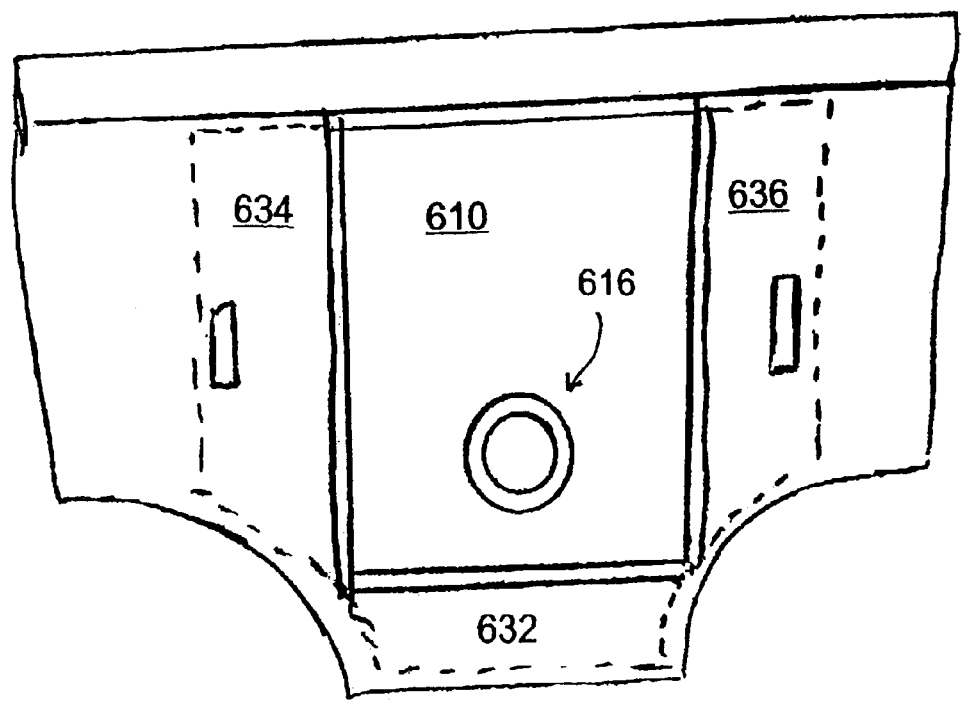
FIG. 11 is an inside plan view of a diaper and undergarment system according to a sixth embodiment of the invention.

Referring now to FIG. 11, a leak control system 650 according to a sixth embodiment of the invention is shown. The system 650 includes a diaper 610, and a specialized undergarment 630 which removably receives the diaper 610 therein.

The diaper 610 in this embodiment is similar to the diaper 10 of the first embodiment, with slightly larger side flanges. The diaper 610 is provided with a sleeve 616, in a manner similar to the diaper 10 of the first embodiment.

The side flanges in the diaper 610 have absorbent material contained therein, and are designed to slidably fit into side pockets 634, 636 provided in the front section of the undergarment 630. The undergarment 630 is also provided with a central pocket 632 to receive a lower portion of the diaper 610 therein.

Seventh Embodiment

Figure 12:
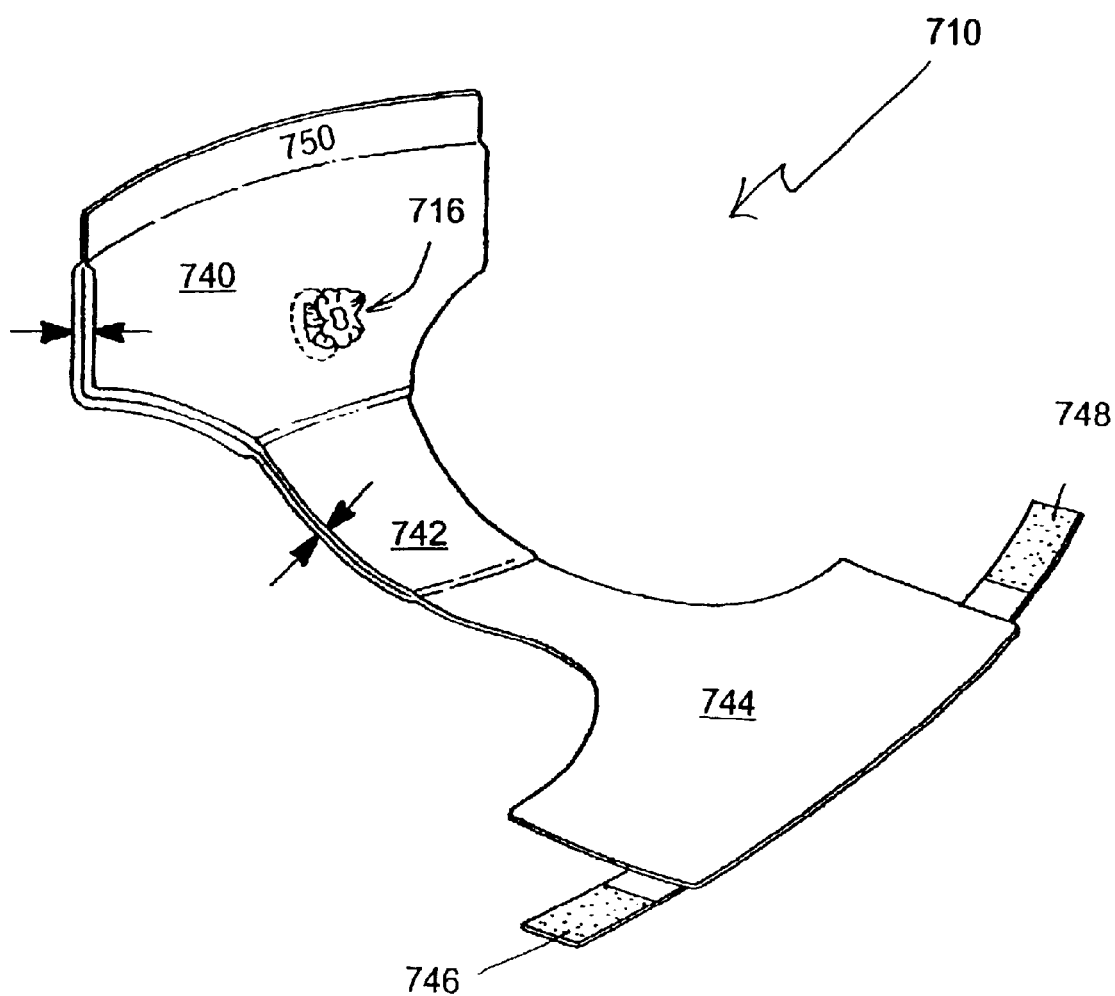
FIG. 12 is a perspective view, partially cut away, of a diaper according to a seventh embodiment hereof.

Referring now to FIG. 12, a diaper 710 according to a seventh embodiment of the invention is shown. The diaper 710 of this embodiment is not intended to be used with an undergarment, but instead, the diaper 10 of the seventh embodiment is intended to be used in place of a normal undergarment. The diaper 710 includes a sleeve 716 similar to the sleeve 16 described in connection with the first embodiment The diaper 710 includes a front upper portion 740, including the sleeve 716. The front upper portion 740 is provided for placement in front of a user, and it includes a double thickness of absorbent material therein, as shown between the opposed arrows in the cut away side portion thereof.

The diaper 710 also includes a front lower portion 742 attached to the front upper portion 740. The front lower portion 742 includes a single thickness of absorbent material therein, as shown between the opposed arrows in the cut away side portion thereof The diaper 710 also includes a back portion 744 attached to the front lower portion 742. The back portion 744 is provided for placement behind a user, and it may include either a single thickness of absorbent material, or may simply be made of flexible plastic and not include any absorbent material. As yet another alternative, the back portion 744 may include a single thickness of absorbent material on the inside surface thereof for placement against the skin of a user. The back portion 744 has a pair of adhesive strips 746, 748 attached to opposite side edges thereof with peel-away protective material thereon, for allowing attachment to an upper waistband 750 of the front upper portion 740, to convert the diaper 710 into a wearable garment.

Although the present invention has been described herein with respect to a limited number of presently preferred embodiments, the foregoing description is intended to be illustrative, and not restrictive. Those skilled in the art will realize that many modifications of the preferred embodiment could be made which would be operable. All such modifications, which are within the scope of the claims, are intended to be within the scope and spirit of the present invention.

Having, thus, described the invention, what is claimed is:

1. A disposable diaper, comprising:
a main diaper body, comprising a flexible plastic housing having a front wall and a back wall sealably joined to the front wall and being substantially parallel thereto, said back wall having an aperture formed therein, said front and back walls cooperating to define a housing chamber therebetween;
said main diaper body further comprising at least one layer of absorbent material disposed within said housing chamber; and
a flexible sleeve attached to the back wall of said housing and surrounding said aperture, said flexible sleeve comprising an outer end portion which is spaced away from said main diaper body and which is substantially free from exposed adhesive material, wherein said flexible sleeve is in fluid communication with said housing chamber.

2. The diaper of claim 1, further comprising an adhesive material attached to a lower portion of the housing front wall.

3. The diaper of claim 1, wherein the main diaper body comprises a first flange extending outwardly at an upper left portion thereof, and a second flange extending outwardly at an upper right portion thereof.

4. The diaper of claim 3, further comprising a fastener attached to each of said first and second flanges for fastening the diaper to a garment.

5. The diaper of claim 1, wherein the sleeve comprises an elastic material.

6. A disposable diaper, comprising:
a main diaper body, comprising a flexible plastic housing having a front wall and a back wall sealably joined to the front wall and being substantially parallel thereto, said back wall having an aperture formed therein, said front and back walls cooperating to define a housing chamber therebetween;
said main diaper body further comprising at least one layer of absorbent material disposed within said housing chamber; and
a flexible sleeve attached to the back wall of said housing and surrounding said aperture, when said flexible sleeve is substantially cylindrical with a length which is greater than the diameter thereof, is substantially perpendicular to said back wall, and is in fluid communication with said housing chamber.

7. The diaper of claim 6, further comprising an adhesive material attached to a lower portion of the housing front wall.

8. The diaper of claim 6, wherein the main diaper body comprises a first flange extending outwardly at an upper left portion thereof, and a second flange extending outwardly at an upper right portion thereof.

9. The diaper of claim 8, further comprising a fastener attached to each of said first and second flanges for use in fastening the diaper to a garment.

10. The diaper of claim 6, where the sleeve comprises an elastic material.

11. The diaper of claim 6, wherein the main diaper body comprises at least two layers of absorbent material disposed within said housing chamber.

12. A fluid control system for an incontinent male, comprising;
a diaper comprising a main diaper body comprising a flexible plastic housing having a front wall and a back wall sealably joined to the front wall and being substantially parallel thereto, said front and back walls cooing to define a housing chamber therebetween; said main diaper body further comprising at least one layer of absorbent material disposed within said housing chamber; and
a flexible, substantially, cylindrical sleeve attached to the back wall of said housing and in fluid communication with said housing chamber, and an undergarment, comprising a front panel having a center pocket thereon for receiving a lower portion of the main diaper body therein.

13. A fluid control system for an incontinent male, comprising:

a diaper, comprising a main diaper body comprising a flexible plastic housing having a front wall and a back wall sealably joined to the front wall and being substantially parallel thereto, said front and back walls cooperating to define a housing chamber therebetween; said main diaper further comprising at least one layer of absorbent material disposed within said housing chamber; and a flexible sleeve attached to the back wall of said housing and in fluid communication with said housing chamber and an undergarment, comprising a front panel having a center pocket thereon for receiving a lower portion of the main diaper body therein;

wherein the main diaper body comprises a first side flange extending outwardly at an upper right portion thereof, and a second side flange extending outwardly at upper left portion thereof; and wherein the front panel of the undergarment also has a left side pocket and a right side pocket ached thereto for respectively receiving the side flanges thereon to allow temporary and removable installation of the diaper in the undergarment.

14. A fluid control system for an incontinent male, comprising:

a diaper comprising a male diaper body comprising a flexible plastic housing having a front wall and a back wall sealably joined to the front wall and being substantially parallel thereto, said font and back walls cooperating to define a housing chamber therebetween; said main diaper body further comprising at least two layers of absorbent material disposed within said housing chamber, said main diaper body having a first flange extending outwardly at an upper left portion thereof, and a second flange extending outwardly at an upper right portion thereof; and a flexible sleeve attached to the back wall of said housing and in fluid communication with said housing chamber, and an undergarment, comprising a front panel having a center pocket thereon for receiving a lower portion of the main diaper body therein, said undergarment further having a left side pocket for receiving the first flange, and a right side pocket for receiving the second flange.

15. A disposable diaper, comprising a main diaper body having a front upper portion, a front lower portion, and a back portion operatively attached to the front lower portion, the back portion of said main diaper body being attachable to said front upper portion to form an undergarment;

said front upper portion of said main diaper body comprising a flexible plastic housing having a front wall and a back wall sealably joined to the front wall and being substantially parallel thereto, said back wall having an aperture formed therein, said font and back walls cooperating to define a housing chamber therebetween;

said main diaper body further comprising at least one layer of absorbent material disposed within said housing chamber; and a flexible sleeve attached to the back wall of said housing and surrounding said aperture, said flexible sleeve having a length which is greater than the diameter thereof and comprising an outer end portion which is spaced away from said main diaper body and which is substantially free from exposed adhesive material, wherein said flexible sleeve is in fluid communication with said housing chamber.

* * * * *